United States Patent [19]
Gittleman

[11] Patent Number: 5,306,150
[45] Date of Patent: Apr. 26, 1994

[54] DENTAL RAMUS IMPLANT

[76] Inventor: Neal B. Gittleman, 15 Greenway Plz. #1-D, Houston, Tex. 77046

[21] Appl. No.: 924,490

[22] Filed: Aug. 4, 1992

[51] Int. Cl.$^5$ ............................................. A61C 8/00
[52] U.S. Cl. .................................... 433/173; 433/176
[58] Field of Search .............................. 433/173, 176

[56] References Cited

U.S. PATENT DOCUMENTS

| | | | |
|---|---|---|---|
| D. 272,560 | 2/1984 | Pinto et al. | 433/173 X |
| D. 272,561 | 2/1984 | Pinto et al. | 433/173 X |
| 4,062,119 | 12/1977 | Linkow et al. | 433/176 |
| 4,547,158 | 10/1985 | Roberts | 433/176 |
| 4,756,690 | 7/1988 | Roberts | 433/176 |
| 5,052,930 | 10/1991 | Lodde et al. | 433/176 X |

Primary Examiner—Gene Mancene
Assistant Examiner—Nicholas D. Lucchesi
Attorney, Agent, or Firm—Ezra L. Schacht

[57] ABSTRACT

A dental ramus implant consisting of a clamping device which can be used with little or no bone surgery in both a unilateral or bilateral fashion to secure either a fixed or removable prosthesis. The ramus clamp is semi-adjustable and attaches to an intermediate member or meso structure supported by two anterior endosseous fixtures. The overlying teeth are secured by conventional prosthodontic means.

A method of designing this implant for several types of applications and a surgical method of use are outlined.

9 Claims, 8 Drawing Sheets

DENTAL RAMUS IMPLANT

BACKGROUND OF THE INVENTION

The present invention relates to dental prosthetics, and more particularly to dental implant reconstruction.

In Disclosure Document No. 298011, submitted to the PTO on Dec. 17, 1991 there appears much of the material in this specification.

Contemporary implant dentistry makes many attempts to aid the "dental cripple" by utilizing a variety of implant modalities. When dealing specifically with the lower jaw, attempts at reconstruction will usually fall into the following two categories: (1) Endosseous anchorage by either a straight line plate, endosseous cylinders or a ramus frame, and (2) Subperiosteal supporting frameworks which lie on top of the bone. Both of the previously mentioned techniques have serious drawbacks which the present invention strives to overcome.

In the first example, contemporary implant reconstruction suggests at least a three-month healing period before prosthodontic reconstruction can commence. It is an object of the present invention to start and finish both the implantation procedure and dental reconstruction in less than four hours. Limitations in the human anatomy often limit the amount of posterior loading that can be accomplished in the posterior area of the mouth where the greatest chewing forces occur. In some circumstances, no appreciable loading can occur beyond the second premolar. Once the implants have healed sufficiently to begin reconstruction, complex and custom made laboratory procedures must be undertaken in order to complete the reconstruction.

Note that the anterior supporting framework 46 is shown in dashed lines to indicate that it is not part of this invention, may take any of several forms, and is shown to illustrate one embodiment of the method of this invention.

It is an object of the present invention to obviate the need for custom-made prosthodontic bridges or retaining bars and their overlying dentures.

Still another object of the present invention is to utilize pre-fabricated prosthetics whenever possible, making implant-retained prosthetics affordable for the masses.

In the second example mentioned above, the much maligned subperiosteal implant requires extensive laboratory procedures to construct. For a predictably excellent fit, two surgical procedures are required. It is an object of the present invention to allow the clinician to complete the dental reconstruction the patient from start to finish in one sitting.

It is a further object of this invention to provide a clamp which does not interfere with the route of the neurovascular bundle.

It is also possible to apply this invention in the replacement of the condylar process, as outlined in principle in FIG. 8. And, of course, it may be applied in other defective condylar processes, elsewhere in the human anatomy, for which this construction is suitable.

Other objects and advantages will become apparent in the following specification when considered in light of the attached drawings.

DESCRIPTION OF THE PREFERRED EMBODIMENT

Figure 1:
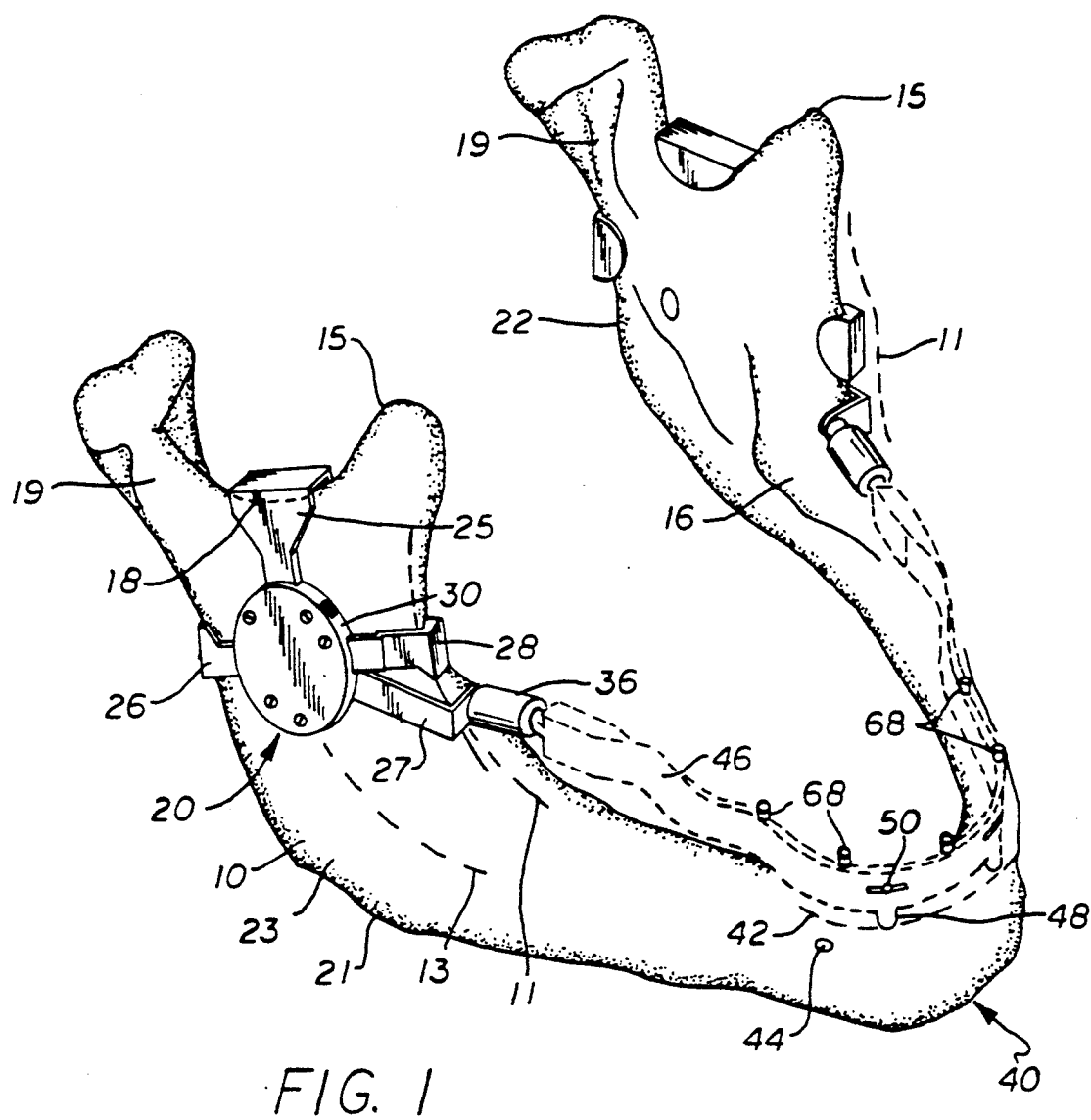
FIG. 1 shows the entire mechanism in place.
Figure 2:
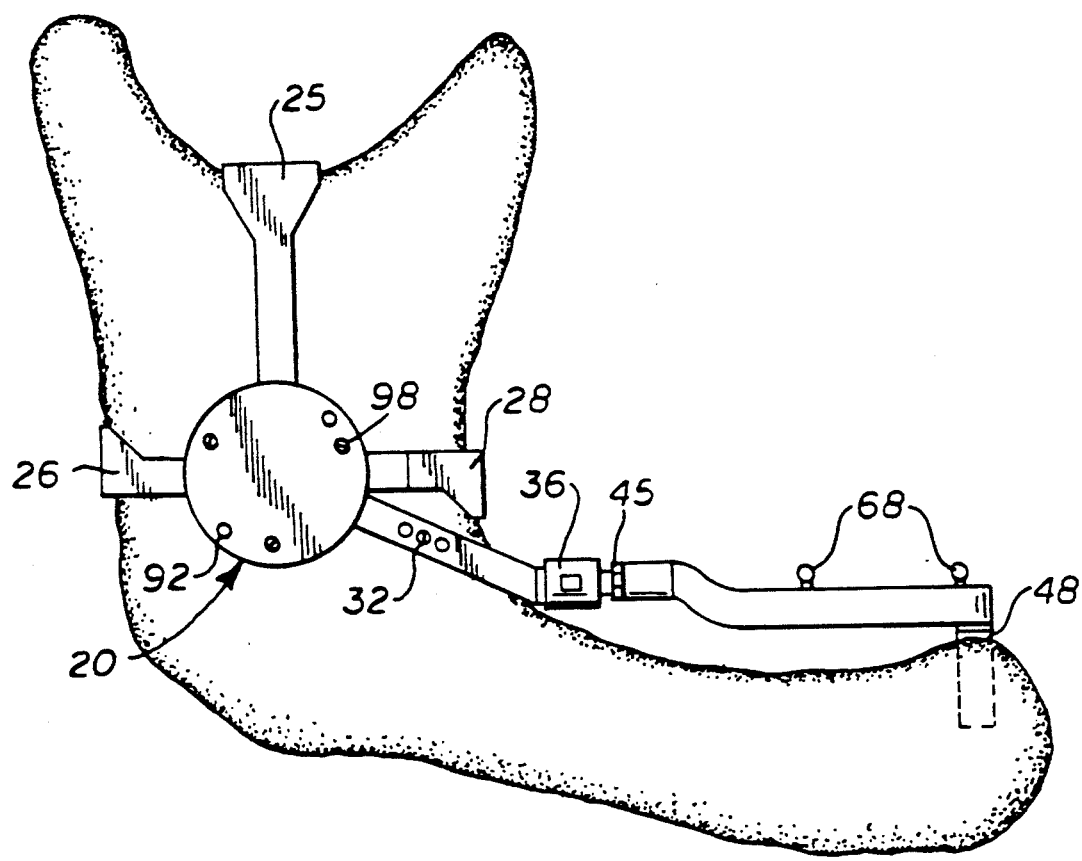
FIG. 2 shows the lateral view of the implant.
Figure 3:
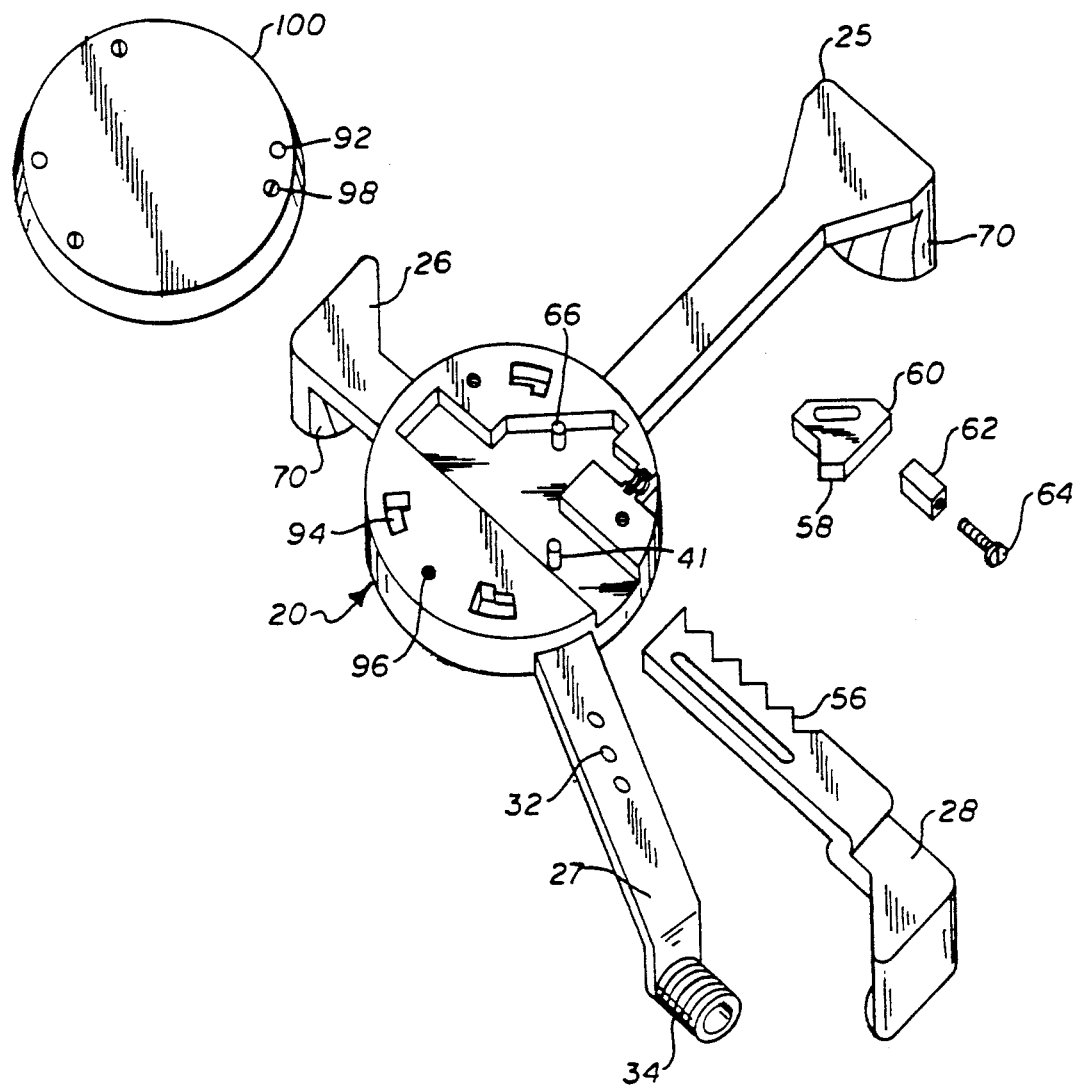
FIG. 3 shows an exploded view of the clamp mechanism with both the cover plate and the locking mechanism removed.
Figure 5:
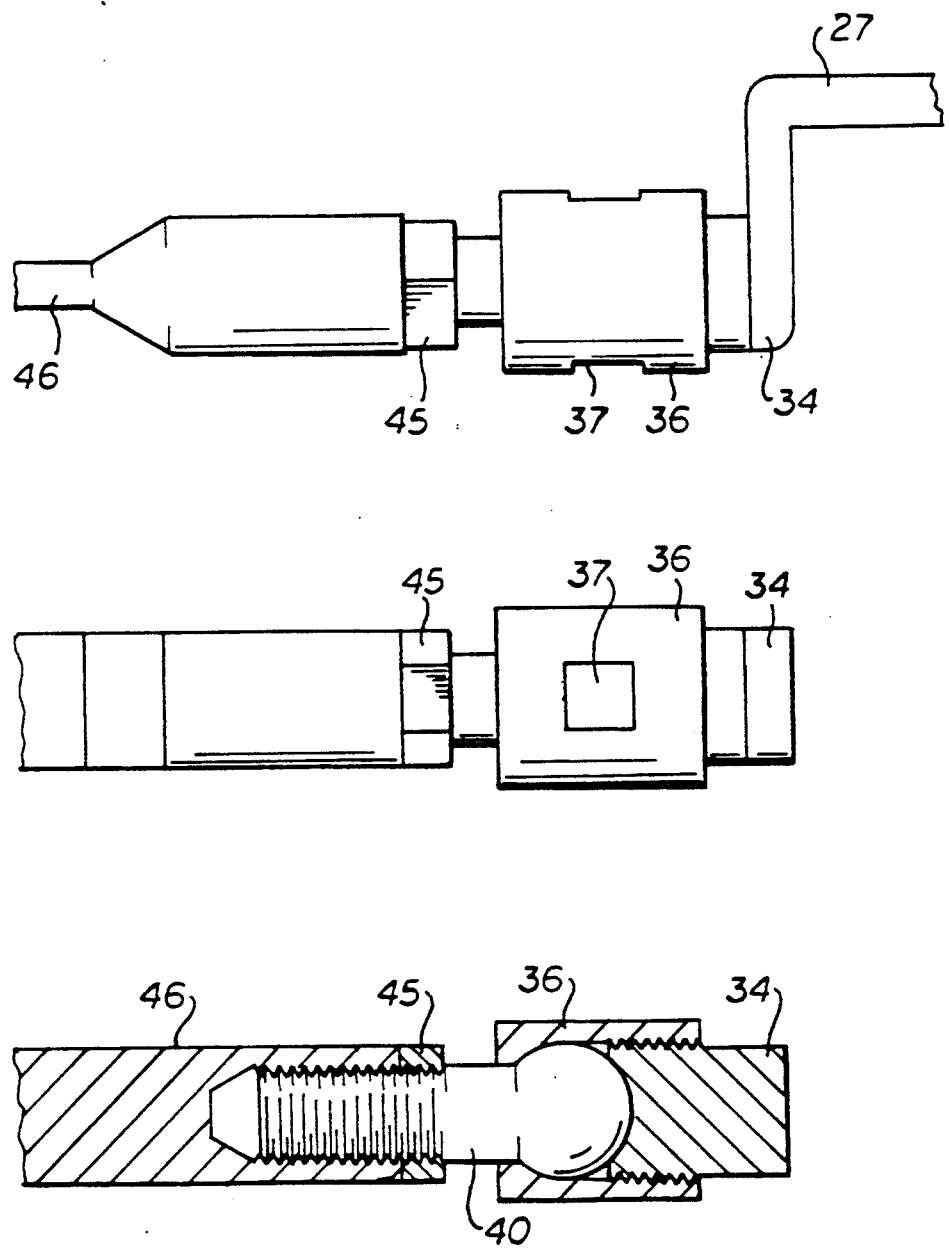
FIG. 5 shows the pivoting ball and sleeve which allows for 6 degrees of freedom in all directions and significant anterior-posterior compensatory movement.

Referring now to the drawings in detail, and in particular to FIGS. 1 and 3 thereof, therein illustrated is a ramus-clamp dental implant designated by the numeral 20. The ramus-clamp 20 is comprised of three non-movable arms. The most superior component will henceforth be referred to as the superior securing arm 25. It is positioned over the sigmoid (or mandibular) notch 18. The posterior securing arm 26 is draped around the posterior aspect of the ramus. Both the superior securing arm 25 and the posterior securing arm 26 are extensions of the main body 30 of the ramus-clamp. Both securing arms lie in the same plane as the anterior articulating arm 27. The anterior articulating arm 27 has three screw holes 32 (or a mechanical equivalent) where fastening screws can be used to further stabilize the main body 30 to the lateral aspect of the ramus. The anterior articulating arm 27 ends in a threaded projection 34 (or a mechanical equivalent) in order to attach to the anterior supporting framework 46 as illustrated best in FIG. 5. Surrounding the threaded projection 34 is a connecting sleeve 36 which will accommodate the ball joint 40 of the anterior supporting framework. The ball joint 40 will allow the anterior supporting framework 46 to align with the anterior articulating arm 27. The end of the ball joint 40 threads into the anterior supporting frame and has a locking nut 45 or similar device to prevent the threaded ball joint from slipping. The connecting sleeve 36 is relieved with 6 facets 37 in order to allow for tightening of the sleeve with a wrench (not shown). Other mechanical parts and methods may be used without departing from the spirit and intent of this invention.

Figure 4:
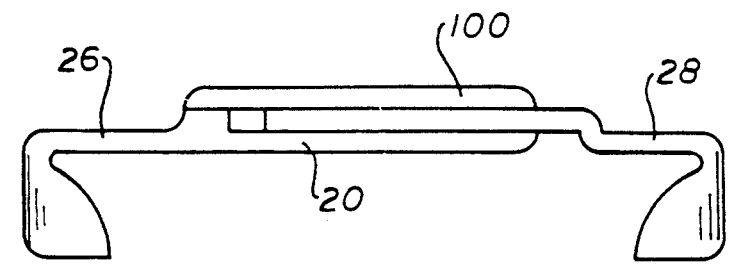
FIG. 4 shows the width of the clamp as well as the complete clamp with the cover exposed.
Figure 4:
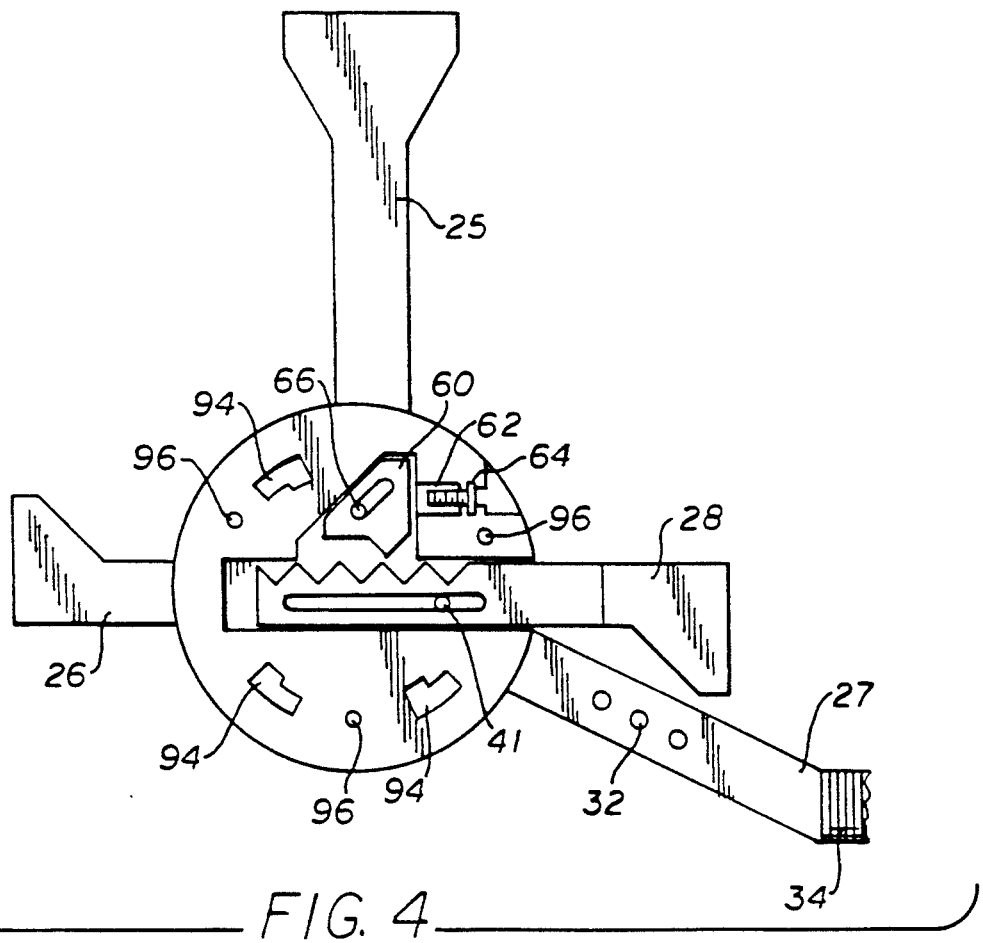

Referring to FIGS. 3 and 4, the anterior securing arm 28 is contained within the ramus clamp assembly 20, and is able to slide in an anterior or posterior direction. A guide pin 41 (or possibly two) or a similar device steadies the anterior securing arm 28 within the confines of the ramus clamp assembly 20. A locking wedge 60 also is present in the ramus clamp assemblage 20. Once the ramus clamp assemlage is positioned during surgery, it is locked by turning the setscrew 64 in clockwise fashion. As the setscrew 64 is turned, it forces a metal spacer 62 to guide the locking wedge 60 into place against the teeth 56 of the anterior securing arm 28. The locking wedge 60 is restrained from parafunctional movement by guide pin 66 or a similar device. The cover plate 100 completes the assembly 20, and is secured to the ramus clamp housing by slightly rotating the outer cover plate 100, and allowing the extruding pins 92 (not shown) to engage the slotted opening marked 94 on the assemblage 20. Fastening screws 98 which screw into the threaded openings 96 complete the locking process for the cover plate 100.

Figure 7:
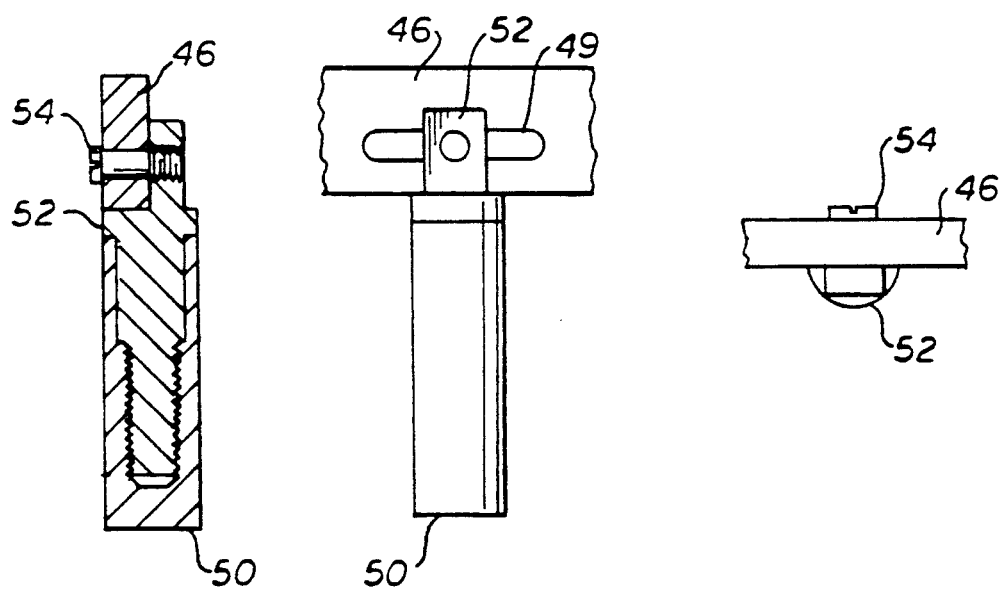
FIG. 7 shows the anterior connection between the frame itself and the anterior anchors.

Referring now to FIG. 7, after both left and right assemblies 20 are placed into their proper positions, the anterior implant supporting frame 46 is secured anteriorly by two conventional cylindrical fixtures 50. Slight surgical descrepancies are compensated for by the long horizontal slots milled into the anterior implant support frame 46. Vertical positioning of the anterior implant support frame 46 can also be adjusted by the vertical movement of the vertically mobile element 52 which threads into the anterior fixtures 50. The anterior support frame 46 is fastened to the vertically mobile element 52. The lower prosthesis (not shown) is fastened by conventional prosthetic means to the implant support frame 46 by the use of "O-Ring" attachments 68.

Figure 6:
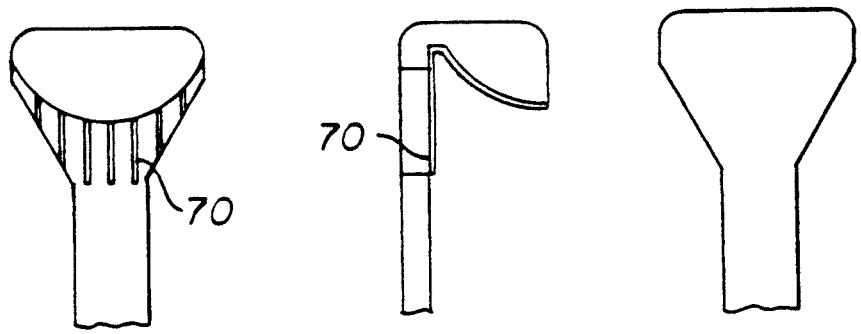
FIG. 6 shows the stabilizing clasps that ride over the area between the condyle and coronoid process, anterior and posterior borders of the ramus.
Figure 6:
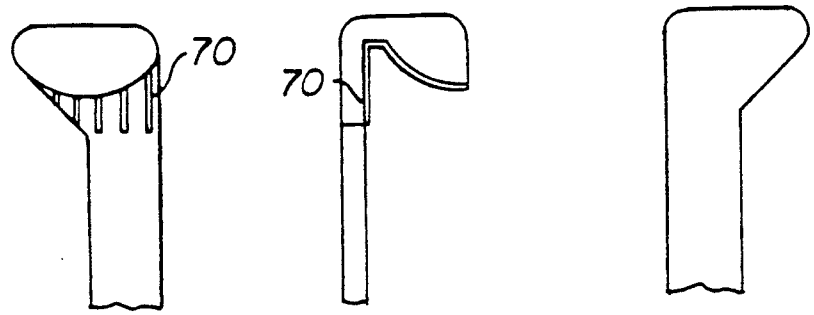
Figure 6:
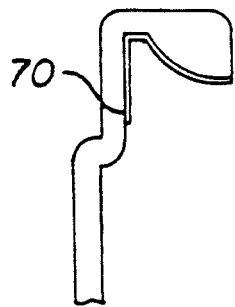

Refer to FIGS. 3 and 6, for a better detail of the ribbed projections 70 which help to prevent slippage of the superior, posterior and anterior (not shown) arms.

Virtually all mechanical connecting devices shown are solely illustrative examples appropriate for the need. Other variations will occur to those skilled in these mechanical arts, the application of which do not affect the claims of this invention.

AN ALTERNATE EMBODIMENT OF THE INVENTION

Figure 8:
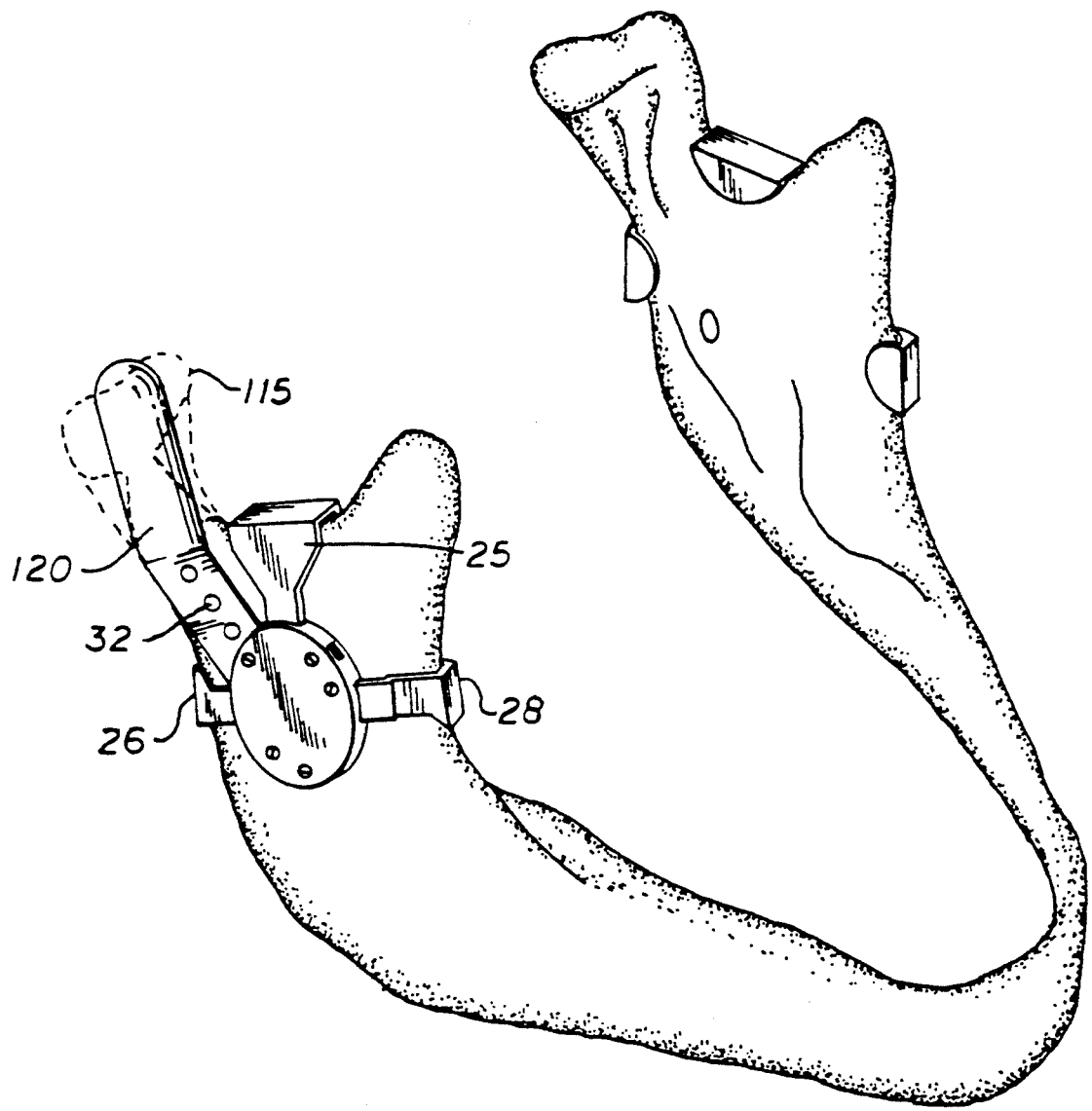
FIG. 8 shows the invention modified for replacement of the condyle or condylar process.

In FIG. 8 is shown an alternate embodiment of the invention, for those problems in which the condyle or condylar process must be rebuilt or replaced. The numbers on the drawing are correlated with those used for the Preferred Embodiment. Portions of the condylar process 115, such as the head, neck, and pterygoid fovea may have deteriorated through disease or from accidental injury. A condylar process arm 120 may be fabricated as a substitute bearing surface for the defective natural condylar process. It may be secured by screws 32, or other equivalent fastening devices, functioning in a manner similar to that of articulating arm 27 in FIG. 1.

It may thus be seen that both embodiments may be used for one patient, in a combined apparatus of FIGS. 1 and 8, should such an unfortunate complication arise.

IMPLANT PLACEMENT PROCEDURE AND TECHNIQUE

Patient is placed in a supine position, and the mouth and perioral structures are prepped and draped in a sterile fashion. Patient will then be intubated for the delivery of a general anesthetic which will be administered via the nasotracheal airway by an anesthesiologist. The oral cavity will then be entered and a throat pack will be placed. The left mandibular ramus 10 is the first area to be exposed and xylocaine with epinephrine 1/100,000 concentration will be infiltrated along the ascending and lateral aspect of the ramus 10. After awaiting onset of adequate hemostasis, a 4.0 cm length incision will be made through the mucosa, utilizing electrocautery in the region of the external oblique ridge 11. Dissection will be carried down through the subcutaneous tissue until the periosteum is encountered. The periosteum is now incised overlying the external oblique ridge 13 and the dissection is carried out in a subperiosteal plane. The ascending ramus will then be exposed from the retromolar region 16 superiorly to the coronoid tip 15. The dissection will continue posteriorly to expose the sigmoid notch 18 with appropriate reflection of tissue within the notch 18. Dissection will then expose the lateral aspect of the mandibular ramus 10 from the condylar neck 19 region to the antegonial notch 21 including the angle of the mandible 23 and inferior border. The previously selected ramus clamp assembly 20 will now be carried to the exposed left site. The superior securing arm 25 and the posterior securing arm 26 are now placed onto the sigmoid notch 18 and the posterior border 22 respectively. Each of the securing arms are placed securely against the bone.

In the event that lateral irregularities of the mandible prevent complete seating, a large bone burr with copious amounts of irrigation will be used to plane down the lateral aspect of the mandible. Attention must be given to the position of the anterior articulating arm 27 before the anterior securing arm 28 is locked into position. The anterior articulating arm 27 must exit the wound in the appropriate plane. Strict attention must be paid at all times during the positioning of the anterior securing arm 28 to prevent displacement. After the clamp is seated and locked into place, the wound will need to be irrigated once again with copious amounts of sterile saline, and packed with a moist gauze pack.

The identical procedure will then need to be carried out on the right mandibular ramus. During the placement of the right ramus clamp, attention is given so that the anterior articulating arm 27 aligns in an analogous fashion with the previously placed left articulating arm 27. Once again, after the clamp is seated and locked into place, the wound will need to be irrigated with copious amounts of sterile saline, and packed with a moist gauze pack.

Attention is then drawn to the anterior mandible 40. Xylocaine with epinephrine 1/100,000 concentration or its equivalent is infiltrated into the anterior region. A mid-crestal incision 42 is then made in the attached mucosa from the left to right mental areas 44, exposing the superior aspect of the mandibular alveolar crest 42. A surgical template (not illustrated) or the anterior supporting frame 46 will then need to be positioned in order to align the anterior fixtures 48 with the anterior supporting frame 46. Any bony irregularities should be removed prior to the initial operation of the pilot drill; furthermore, the alveolar crest may be flattened, if indicated. The anterior endosseous fixtures 48 are then placed in accordance with conventional techniques.

After placement, the connecting elements 50 will need to be inserted into the anterior fixtures. Once a visual confirmation of fit has been achieved, all wounds would be re-irrigated with sterile saline and the commencement of suturing, utilizing 3.0 chromic in a continuous fashion, will occur. The patient, at this time, is now turned over to the care of the prosthodontist, who will then fasten the implant support frame 46 to both articulating arms 27 and to both anterior fixtures 48. Following frame placement, the pre-fabricated lower denture (not shown) is tried in place. In accordance with accepted prosthodontic procedures, the denture would then be luted to its foundation and secured by means of light cured acrylic. The throat pack would now be removed and the hypopharynx suctioned clear. The patient would be extubated in the operating room and taken to recovery.

What is claimed is:

1. A clamp securable non-invasively to the ramus portion of the human mandible, the clamp having means for engagement with clampable surfaces of said ramus portion, said clamp further having an anterior articulating arm, support means for the jawbone, said arm having connecting means adaptable to the support means selected for the jaw bone, the clamp further comprising:
   a generally thin central hub, the hub adapted to be positioned appropriately on said ramus portion;
   radiating from said hub,
      (1) two fixed securing arms, comprising a superior securing arm and a posterior securing arm;
      (2) said anterior articulating arm terminating in said connecting means; and
      (3) an adjustable anterior securing arm;
   said hub having
      (a) means to secure said superior securing arm on a clampable surface of the mandibular notch of said ramus;
      (b) means to secure said posterior securing arm within the posterior border of said ramus; and
      (c) means to secure said anterior articulating arm to a clampable surface within the anterior border of said ramus.

2. A clamp as recited in claim 1, in which said posterior border of said ramus portion is defined to include the area known as the angle.

3. A clamp securable to the ramus portion of the human mandible, the mandible having a defect in that portion of said mandible defined as the condylar process, the clamp having means for engagement with clampable surfaces of said ramus portion, said clamp further having condylar process means suitable as replacement means for at least that defective portion of said condylar process of the patient, the clamp further comprising:
   a generally thin central hub, the hub adapted to be positioned appropriately on said ramus;
   radiating from said hub,
      (1) two fixed securing arms, comprising a superior securing arm and a posterior securing arm;
      (2) an arm adapted to be adjacent to and to follow the posterior border of said ramus portion and terminating in a portion simulating the defective portion of said condylar process of said patient;
      (3) an adjustable anterior securing arm;
   said hub having
      (a) means to secure said superior securing arm within the clampable surface of the mandibular notch of said ramus portion;
      (b) means to secure said posterior securing arm within the posterior border of said ramus portion; and
      (c) means to secure said adjustable anterior securing arm within the anterior border of said ramus portion.

4. A method of non-bone-invasively installing a clamp securable to the ramus portion of the human mandible, the clamp having a superior securing arm, an anterior securing arm and a posterior securing arm, said clamp further having an anterior articulating arm and support means for the jaw bone, said anterior articulating arm having connecting means adaptable to the support means selected for the jaw bone, the steps in the method comprising:
   a. Exposing said mandibular ramus, by incising through the mucosa in the area of the external oblique ridge;
   b. Exposing the ascending portion of said ramus from the retromolar region superiorly to the coronoid tip;
   c. Dissecting posteriorly to expose the sigmoid notch of said ramus and uncovering the lateral aspect of the ramus while exposing the angle of said mandible and its inferior border;
   d. Placing both said superior and said posterior securing arms onto said sigmoid notch and posterior border respectively; and
   e. Seating said clamp into position, and then locking said clamp in place.

5. A method of securing a clamp to the external contour of the ramus portion of the human mandible without cutting cavities within said ramus portion for said securing, the method comprising:
   a. selecting at least two generally parallel and opposite portions of said external contour of said ramus portion, said portions being clampable by said clamp;
   b. selecting appropriate means of attachment to said clamp, said attachment means being adaptable for replacement of a defective portion of said mandibular element; and
   c. clamping said clamp around at least a part of said generally parallel and opposite portions of said external contour of said ramus portion without invading the structure of said ramus portion.

6. A method of securing a clamp to the external contour of the ramus portion of the human mandible as recited in claim 5, said attachment means being adaptable for replacement of at least defective portions of the jawbone.

7. A method of securing a clamp to the external contour of the ramus portion of the human mandible as recited in claim 5, said attachment means being adaptable for replacement of at least defective portions of the condylar process.

8. A method of securing a clamp to the external contour of the ramus portion of the human mandible as recited in claim 5, further comprising the step of securing said clamp between the sigmoid (mandibular) notch and the angle of the ramus portion.

9. A method of securing a clamp to the external contour of the ramus portion of the human mandible as recited in claim 6, said attachment means being adaptable for replacement of at least a part of a defective condylar process.

* * * * *